United States Patent [19]
Takekawa

[11] Patent Number: 4,483,927
[45] Date of Patent: Nov. 20, 1984

[54] METHOD OF AUTOMATICALLY ANALYZING CHEMICAL SUBSTANCES AND AN AUTOMATIC CHEMICAL ANALYZER

[75] Inventor: Hiroshi Takekawa, Kunitachi, Japan
[73] Assignee: Olympus Optical Co., Ltd., Tokyo, Japan
[21] Appl. No.: 254,489
[22] Filed: Apr. 15, 1981
[30] Foreign Application Priority Data
Apr. 18, 1980 [JP] Japan ................................. 55-50254
[51] Int. Cl.³ ..................... G01N 35/02; G01N 35/04; G01N 35/06
[52] U.S. Cl. .................................... 436/43; 364/497; 422/63; 422/64; 422/65; 422/67; 422/100; 436/47; 436/48
[58] Field of Search ................ 23/230 R; 422/64, 65, 422/67; 364/497, 498; 436/43, 47, 48, 100

[56] References Cited
U.S. PATENT DOCUMENTS

| | | | |
|---|---|---|---|
| 3,533,744 | 10/1970 | Unger | 422/65 |
| 3,825,410 | 7/1974 | Bagshawe et al. | 422/66 |
| 3,917,455 | 11/1975 | Bak et al. | 422/65 X |
| 3,985,507 | 10/1976 | Litz et al. | 422/65 |
| 4,039,286 | 8/1977 | Keller et al. | 436/47 |
| 4,058,367 | 11/1977 | Gilford | 422/63 |
| 4,066,412 | 1/1978 | Johnson et al. | 422/65 |
| 4,224,032 | 9/1980 | Glover et al. | 422/65 |

Primary Examiner—Michael S. Marcus
Attorney, Agent, or Firm—Parkhurst & Oliff

[57] ABSTRACT

An automatic chemical analyzer for measuring quantitatively a plurality of kinds of substances of a number of sample liquids comprises: a reagent delivery unit including a plurality of reagent bottles containing different kinds of reagents which are required for measuring the plurality of kinds of substances and a syringe type dispenser for delivering given amounts of reagents into a plurality of empty reaction vessels set in a cassette, a reaction vessel supply unit for holding a plurality of cassettes and for supplying successively the reaction vessels in which given reagents have been previously delivered in accordance with given test items to be performed, an analyzing unit for receiving the successive reaction vessels from the reaction vessel supply unit and including a syringe type sample delivery pump for supplying given amounts of sample liquids into the reaction vessels and a colorimetric device for measuring colorimetrically test liquids in the reaction vessels, a first control unit for controlling the operation of the reagent delivery unit and a second control unit for controlling the operation of the reaction vessel supply unit in accordance with a given program. In the reagent delivery unit, the reagents are delivered into the reaction vessels in accordance with a program which can be previously determined statistically.

5 Claims, 2 Drawing Figures

METHOD OF AUTOMATICALLY ANALYZING CHEMICAL SUBSTANCES AND AN AUTOMATIC CHEMICAL ANALYZER

BACKGROUND OF THE INVENTION

The present invention relates generally to an automatic chemical analysis for quantifying given chemical substances contained in sample liquids such as blood, urine, etc.

Heretofore, various kinds of automatic chemical analyzers have been proposed and devised. Presently the majority of analyzer models employ a discrete system. In the discrete system there has been proposed a batch system in which given amounts of sample liquids contained in sample cups set in a sampler are successively supplied into reaction vessels which are intermittently fed along a given path; given amounts of a reagent or reagents corresponding to an item or items to be tested are supplied into the successive reaction vessels to cause a given reaction under a controlled temperature to form test liquids; and then the test liquids are successively colorimetered to quantify given substances in the sample liquids. In the discrete system there has been also proposed a bag system in which a plurality of small packs each containing one of the reagents in a predetermined amount is provided. A given amount of sample liquid to be analyzed is introduced into the bag, and a given pack containing a given reagent corresponding to a given test item to be measured is broken by pressing the pack to extrude the relevant reagent in the sample liquid to cause a given reaction to form a test liquid in the bag. Then the test liquid is quantified by means of colorimetry. In the batch system it is necessary to set previously in an analyzer a number of reagents which are required to perform various kinds of tests and also to provide a reagent delivery mechanism for selectively delivering a given reagent in accordance with the test item to be analyzed and thus, the whole analyzer is liable to be complicated and large. Moreover since the time for effecting the reagent delivery is limited by the analyzing operation of the analyzer, accuracy of reagent delivery might be decreased and the dispenser mechanism might be soon worn. Further, if a number of reagents is to be selectively delivered by means of a single dispenser, a probe of the reagent dispenser could not be washed or cleaned sufficiently for a limited time of delivery, and a serious problem of contamination between the reagents might occur. Moreover since a number of reagents of different kinds must be set in the analyzer, the analyzer might be soiled by reagents during the reagent delivery.

In the bag system a small number of packs, i.e. reagents, can only be provided in a bag and, thus, freedom of selection of reagents and analyzing processes is limited to a great extent. Therefore, it is quite inconvenient for a user who wants to perform a variety of analyzing processes using a number of reagents of different kinds. Moreover, usually only one reagent in a bag is used for respective measurement, and the remaining reagents are wasted without being used, so that the cost of analysis is unduly increased. Further, the wasted bags can be treated only with difficulty.

SUMMARY OF THE INVENTION

The present invention has for its object to provide a novel and useful method of automatically analyzing chemical substances contained in sample liquids, in which method the above mentioned drawbacks of the known methods can be effectively obviated and a number of desired test items can be measured in an accurate and prompt manner.

It is another object of the invention to provide a method of automatically analyzing chemical substances, in which any emergency test can be easily interrupted in a routine analysis, any desired kind of reagents can be used at will, and the reagents are hardly wasted.

According to the invention, a method of automatically analyzing chemical substances contained in sample liquids comprises: a step of delivering given amounts of reagents of different kinds, required to measure the substances of different kinds, into a number of reaction vessels set in a plurality of cassettes; a step of stocking a reaction vessel supply unit with a plurality of cassettes each comprising a plurality of reaction vessels containing the given amounts of the given reagents; a step of selecting successive reaction vessels stocked in the reaction vessel supply unit in accordance with substances to be measured for successive sample liquids, in said selected reaction vessels the given reagents having been previously delivered; a step of supplying successively the selected reaction vessels into an analyzing unit; a step of delivering successively given amounts of the sample liquids into the reaction vessels successively supplied into the analyzing unit; a step of allowing given reaction in the successive reaction vessels to form successive test liquids; and a step of measuring the successive test liquids to quantify the given substances in the successive sample liquids.

The present invention also relates to an automatic chemical analyzer and it is still another object of the invention to provide a novel and useful automatic chemical analyzer in which a reagent delivery mechanism can be operated independently from an analyzing unit and thus, can be constructed by a simple mechanism, the analyzing unit can perform desired measurements in an accurate and prompt manner, and the analyzing unit can be hardly soiled by the reagents.

According to the invention, an automatic chemical analyzer comprises: an analyzing unit for supplying a given amount of sample liquid into a reaction vessel containing a given amount of a reagent corresponding to a test to be performed for the relevant sample liquid and for quantifying a given substance contained in the sample liquid; a reagent delivery unit including a plurality of reagent bottles for containing different kinds of reagents corresponding to different kinds of tests and a reagent delivery mechanism for delivering given amounts of reagents contained in the bottles into a number of reaction vessels contained in a plurality of cassettes; a reaction vessel supply unit for holding movably a plurality of cassettes each of which includes a plurality of reaction vessels containing the given amounts of the reagents, for selecting a reaction vessel which contains a given reagent in accordance with the test item to be measured in the analyzing unit, and for supplying the selected vessel into the analyzing unit; and control means for controlling the reagent delivering unit in accordance with a program which is independent from an analyzing program in the analyzing unit.

The present invention is based on a recognition that test items and the number of sample liquids to be measured in a day can be experimentally predetermined and, thus, given reagents corresponding to the test items to be measured in a day can be previously introduced or delivered into reaction vessels to be used in a day in accordance with the test items and the number of sample liquids to be treated in a day.

EXPLANATION OF THE PREFERRED EMBODIMENTS

Figure 1:
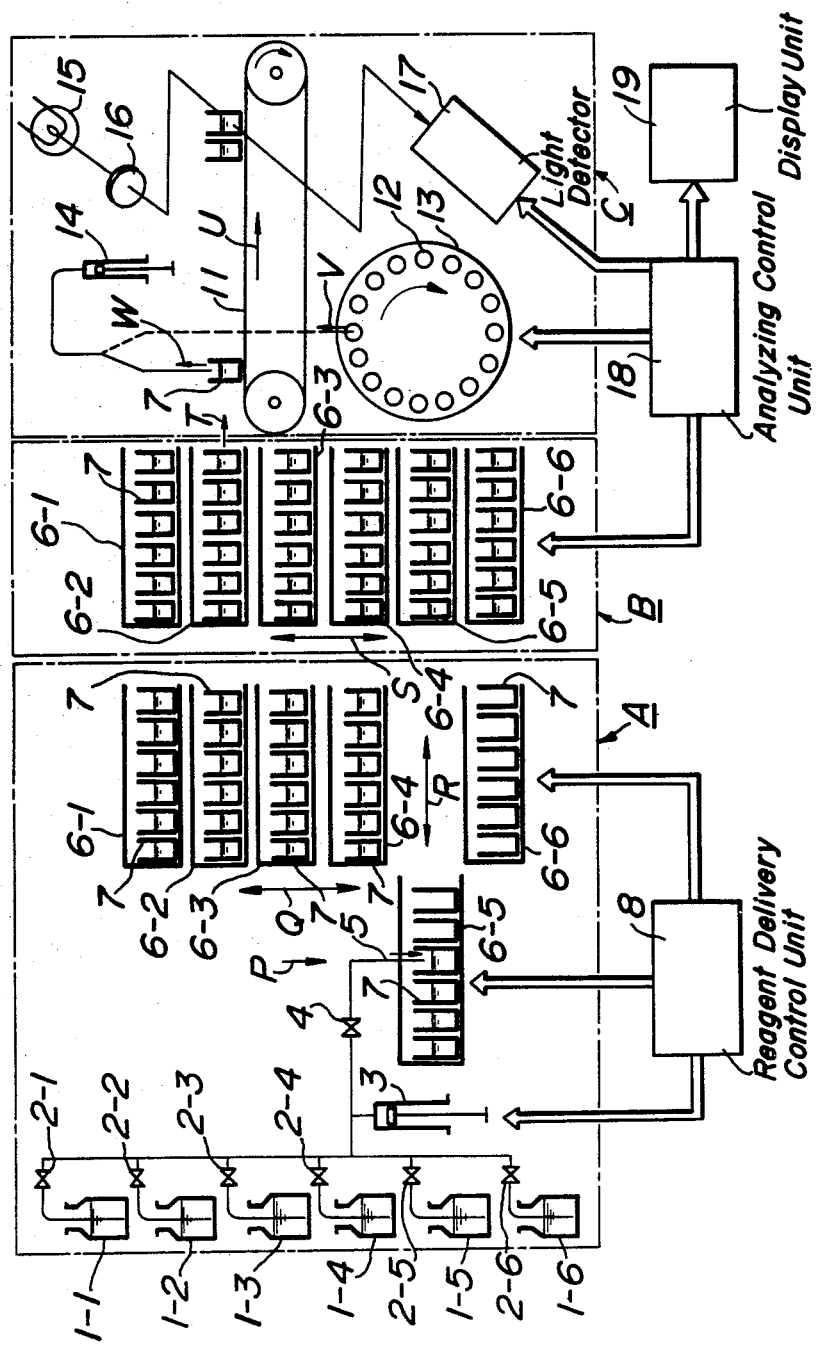
FIG. 1 is a schematic diagram showing an embodiment of the automatic chemical analyzer according to the invention.

FIG. 1 shows schematically an embodiment of the automatic chemical analyzer according to the invention. The analyzer comprises a reagent delivery unit A, a reaction vessel supply unit B which is detachably provided with respect to the reagent delivery unit A in the present embodiment, and an analyzing unit C which is mechanically coupled with the reaction vessel supply unit B. Now the construction and operation of these units will be explained in detail.

REAGENT DELIVERY UNIT A

In the reagent delivery unit A there are provided six reagent bottles 1-1, 1-2, . . . 1-6 containing different kinds of reagents. These bottles 1-1 to 1-6 are commonly connected through respective valves 2-1 to 2-6 to a syringe type pump 3 which is then connected through a valve 4 to a probe 5 an outlet of which is arranged at a given reagent delivery position P. In the reagent delivery unit A there can be arranged six cassettes 6-1 to 6-6 which are supported movably up and down as illustrated by a vertical double-headed arrow Q. Further at a level of the reagent delivery position P any one of the cassettes can be moved right and left also as shown by a horizontal double-headed arrow R. In each of the cassettes 6-1 to 6-6 are removably set a number of reaction vessels 7, in the present embodiment six reaction vessels. In the reagent delivery unit A, a given amount of the first reagent contained in the first bottle 1-1 is delivered into each of six reaction vessels 7 in the first cassette 6-1, a given amount of the second reagent in the second bottle 1-2 is supplied into six reaction vessels 7 in the second cassette 6-2 and so on. In case of delivering a given amount of the fifth reagent contained in the fifth reagent bottle 1-5 into six reaction vessels 7 installed in the fifth cassette 6-5, the fifth cassette 6-5 is selected and is moved into the reagent delivery position P under the probe 5 and after the valve 2-5 is opened and the valve 4 is closed, the syringe pump 3 is driven to draw the given amount of the fifth reagent. Then the valve 2-5 is closed and the valve 4 is opened and a piston of the syringe pump 3 is pushed into a cylinder by a given stroke to dispense the given amount of the fifth reagent into a first reaction vessel 7 in the fifth cassette 6-5 via the probe 5. The above operation is repeated while the cassette 6-5 is moved horizontally as shown by the arrow R in an intermittent manner by a given pitch corresponding to a pitch of the reaction vessels arranged in the cassette 6-5. In this manner the given amount of the fifth reagent can be delivered into the six reaction vessels 7 in the fifth cassette 6-5. It should be noted that during this delivery of the fifth reagent the valves 2-1 to 2-4 and 2-6 are kept closed. In a similar manner, the different reagents can be selectively delivered into the reaction vessels in the different cassettes 6-1 to 6-5. The above mentioned operation of the reaction delivery unit A is controlled by instructions supplied from a reagent delivery control unit 8 in which analysis data such as test items and the number of samples have been previously entered.

REACTION VESSEL SUPPLY UNIT B

The reaction vessel supply unit B receives the cassettes 6-1 to 6-6 including the reaction vessels in which the reagents have been delivered. In this unit B the cassettes 6-1 to 6-6 can be moved up and down as shown by a double-headed arrow S. Any one of cassettes is selected in accordance with an analyzing program in the analyzing unit C and the selected cassette is moved into a level of supplying position T and at least one reaction vessel 7 contained in the relavent cassette can be then supplied into the analyzing unit C. Since the supply of the reaction vessel 7 into the analyzing unit C is controlled in accordance with the analyzing program in the analyzing unit C, in one case the reaction vessels 7 in the same cassette will be successively supplied into the unit C, but in another case the reaction vessels 7 contained in different cassettes will be successively delivered into the unit C.

ANALYZING UNIT C

The analyzing unit C comprises a reaction vessel feed mechanism 11 for transporting the reaction vessel 7 supplied from the reaction vessel supply unit B along a given path in a direction shown by an arrow U. The unit C further comprises a sampler 13 for holding a number of sample cups 12 containing sample liquids such as bloods extracted from patients and for rotatably indexing any one of sample cups at a sample sucking position V at which position a given amount of sample liquid is sucked by a sample delivery mechanism 14. The sucked sample liquid is then dispensed at a delivery position W into a reaction vessel 7 on the feed path. While the vessel 7 is transported by the feed mechanism 11, the sample liquid in the vessel is mixed with the given reagent which has been previously supplied into the vessel. The mixed liquid thus formed is heated to a given temperature for a given time to cause a reaction. A test liquid is formed in the vessel 7. The test liquid is then colorimetrically measured by a photoelectric colorimeter including a light source 15, an interference filter 16 and a light detector 17. In this embodiment a so-called direct measurement is carried out and the test liquid is measured while being retained in the vessel 7. After the measurement, the reaction vessel 7 is removed from the feed mechanism 11 by means of a suitable mechanism not shown. The above operation of the analyzing unit C is controlled by commands supplied from the control unit 18 in accordance with the analyzing program which has been previously entered into the unit 18. The control unit 18 further receives an output signal from the light detector 17 of the colorimeter and suitably uses the signal to produce analytic results which are displayed by a display unit 19 or printed out by a printer not shown.

As explained above, in the analyzer of this embodiment there are provided the reagent delivery unit A and the analyzing unit C in a mechanically separable manner and these units A and C are controlled independently from each other by means of the control units 8 and 18, respectively. Therefore, the time required for delivering the reagents could not be limited by the analyzing program of the analyzing unit C, so that the reagent delivery mechanism may be of a reasonable type and the delivery accuracy and wearability can be improved. Further, the reagent delivery unit A and the analyzing unit C may be settled separately from each other, so that the freedom of arrangement can be made high. Further, since the analyzing unit A does not comprise the reagent delivery mechanism, the unit A can be made simple in construction and small in size. Moreover, the analyzing unit A could hardly be soiled by the reagents and the speed of analysis can be materially increased. Furthermore, the test items can be simply changed and an emergency analysis can be easily interposed in a routine analysis. Therefore, many different kinds of test items may be selected for a single test body, if any, and the same test item may be measured for successive test bodies. It is quite convenient that respective test bodies can be treated for a number of test items other than the routine analysis. Further, the reagents to be used are not limited to exclusive reagents designated by a particular reagent manufacture, but any other reagents supplied by different manufactures can be equally used. As a case may be, reagents manufactured by users may be used and any desired analyzing process may be adopted.

Figure 2:
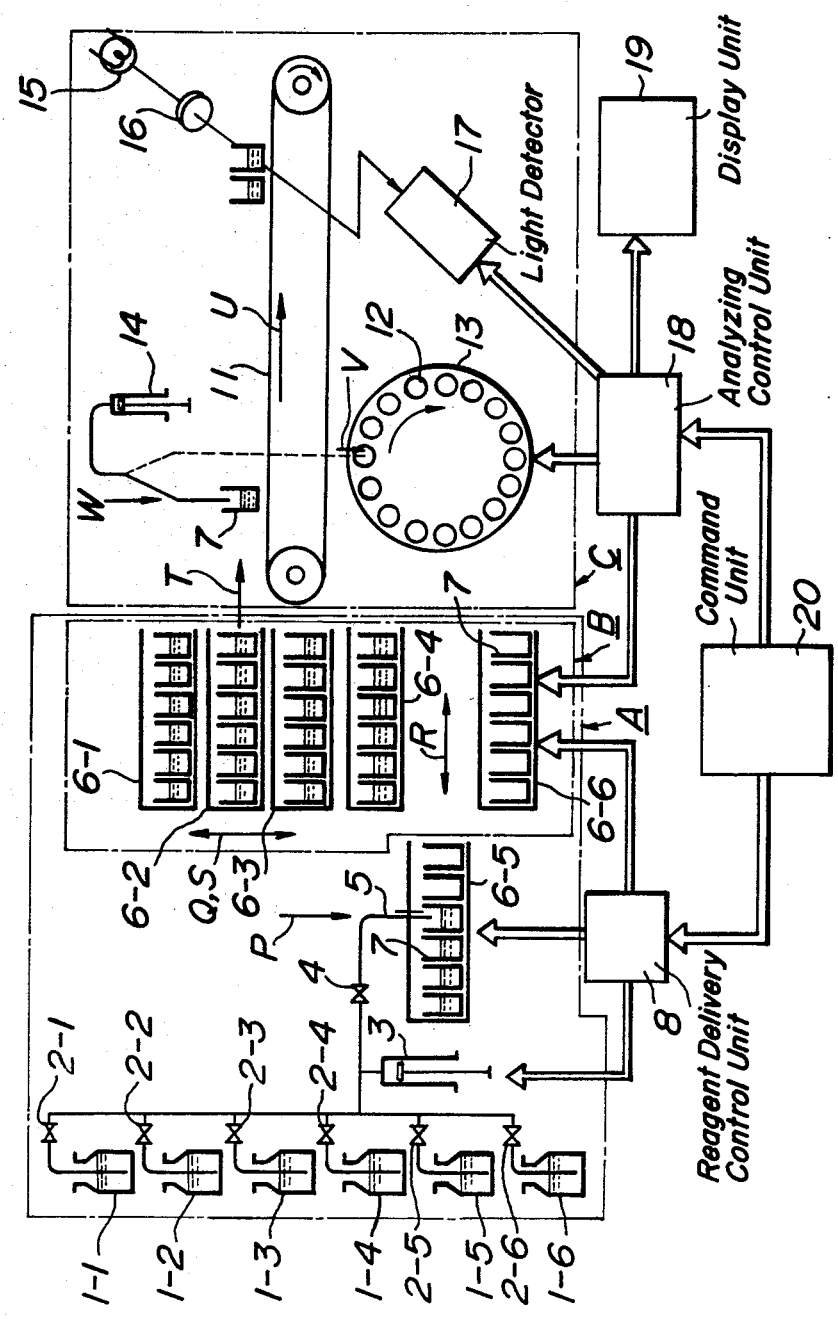
FIG. 2 is a schematic diagram illustrating another embodiment of the automatic chemical analyzer according to the invention.

FIG. 2 is a schematic view showing another embodiment of the automatic chemical analyzer according to the invention. In FIG. 2 portions corresponding to those of the previous embodiment shown in FIG. 1 are denoted by the same reference numerals used in FIG. 1. The analyzer of this embodiment differs from the previous embodiment in that a reaction vessel supply unit B is mechanically coupled with a reagent delivery unit A as well as with an analyzing unit C, and a plurality of cassettes 6-1 to 6-6 set in the reaction vessel supply unit B are movable into the reagent delivery unit A where a given amount of any one of different kinds of reagents can be delivered into a reaction vessel 7, and that there is provided a command unit 20 for totally controlling a reagent delivery control unit 8 and an analyzing control unit 18. An operator can enter given commands into the command unit 20. In the present embodiment, if the reaction vessels, the number of which has been predetermined experimentally in accordance with the number of test items and that of test bodies, have been all used, the analyzing operation is interrupted temporarily by the command unit 20 via the control units 8 and 18, and then any required reagents are delivered into empty reaction vessels 7 in the previously set cassettes or into vessels set in newly installed cassettes. In this manner it is possible to supplement any required reaction vessels containing given reagents in a simple manner without requesting manual operation. In the present embodiment, since the reagent delivery unit A, reaction vessel supply unit B and analyzing unit C are mechanically coupled with each other, the whole units must be installed at one place and thus, the freedom of arrangement is not attained. However, the remaining advantages achieved by the previous embodiment can be obtained as they are.

The present invention is not limited to the embodiments explained above, but may be modified in various ways within the scope of the invention. For instance, the number of the cassettes set in the reaction vessel supply unit B, the number of the reaction vessels set in a single cassette and the number of the reagents of different kinds are not limited to six, but may be of any desired number other than six. As the analyzing unit C, use may be made of any one of known analyzers. For instance, there may be provided a number of interference filters 16 and any one of them may be selectively inserted into an optical path or more than two filters may be used for each test liquid to effect a multiple wavelength colorimetric measurement.

As explained above in detail, since according to the invention the reagent delivery unit is separated from the analyzing unit, these units are controlled separately from each other in such a manner that in the reagent delivery unit given amounts of different kinds of reagents are previously delivered into a number of reaction vessels set in the cassettes in accordance with the test items to be measured, which can be experimentally predetermined, and in the analyzing unit the reaction vessels containing the reagents required for conducting the desired measurement are selectively extracted from the reaction vessel supply unit so as to perform given analyses. Therefore, the various drawbacks of the known automatic chemical analyzers can be effectively removed and the required analyses can be carried out in an accurate and prompt manner.

What is claimed is:

1. A method of automatically analyzing chemical substances of different kinds contained in a number of sample liquids comprising the steps of:
   (a) delivering a given amount of a reagent selected from a plurality of reagents of different kinds, required to measure the substances of different kinds, into each of a plurality of reaction vessels in each of a plurality of reaction vessel cassettes by means of a reagent delivery unit, whereby a plurality of cassettes, each containing a plurality of reaction vessels filled with the same reagent, is prepared prior to sample addition and analysis in said filled reaction vessels;
   (b) stocking a reaction vessel supply unit with a plurality of said cassettes, each cassette containing a plurality of reaction vessels into which the same reagent has been delivered;
   (c) selecting in any sequence any one of the cassettes stocked in the reaction vessel supply unit and containing a plurality of reaction vessels containing a reagent related to the substance to be measured for a sample liquid by displacing said cassette into a reaction vessel removal position while said cassette is maintained in said supply unit;
   (d) removing and supplying a reaction vessel from the selected cassette into an analyzing unit;
   (e) delivering a given amount of the sample liquid from a sampler in the analyzing unit into the reaction vessel supplied into the analyzing unit;
   (f) allowing a given reaction to proceed in the reaction vessel to form a test liquid;
   (g) measuring the test liquid contained in the reaction vessel to quantify the given substance in the sample liquid; and
   (h) repeating said steps (c) to (g) for successive sample liquids, while said step (a) of delivering the reagent is controlled independently from the step (e) of delivering the sample liquid, in the course of which repetition, at least one cassette is selected while a previously selected cassette still contains at least one reaction vessel and remains in said supply unit.

2. A method according to claim 1, wherein said analyzing unit operates independently of said reagent delivery unit.

3. A method according to claim 1, wherein said reagent delivering step is controlled by a program which has been statistically predetermined in accordance with an analyzing operation to be performed in a day.

4. A method according to claim 1, wherein said reagent delivering step is controlled by a program which is different and independent from a program by means of which said reaction vessel selecting step, reaction vessel supplying step, sample liquid delivering step and measuring step are controlled.

5. A method according to claim 1, wherein said reagent delivering step and the reaction vessel supplying step are performed by a partially common mechanism for driving the cassettes and are controlled by a program for supplementing reaction vessels containing a given reagent while the reaction vessel supplying step and the sample liquid delivering step in the analyzing unit are interrupted temporarily.

* * * * *